United States Patent [19]

Kauvar et al.

[11] Patent Number: 5,587,293
[45] Date of Patent: Dec. 24, 1996

[54] METHOD TO IDENTIFY BINDING PARTNERS

[75] Inventors: Lawrence M. Kauvar, San Francisco; Hugo O. Villar, Newark, both of Calif.

[73] Assignee: Terrapin Technologies, Inc., South San Francisco, Calif.

[21] Appl. No.: 177,673

[22] Filed: Jan. 6, 1994

[51] Int. Cl.$^6$ .................................................. G01N 33/53
[52] U.S. Cl. ......................... 435/7.21; 435/7.9; 435/7.93; 436/518; 436/548; 364/413.01
[58] Field of Search .................................. 435/7.9, 7.93, 435/7.21; 436/518, 548, 809, 501, 547; 935/110; 364/413.01

[56] References Cited

U.S. PATENT DOCUMENTS

| | | | |
|---|---|---|---|
| 4,963,263 | 10/1990 | Kauvar | 210/635 |
| 5,133,866 | 7/1992 | Kauvar | 210/635 |
| 5,217,869 | 6/1993 | Kauvar | 435/7.9 |
| 5,300,425 | 4/1994 | Kauvar | 435/7.9 |

FOREIGN PATENT DOCUMENTS 8903430  4/1989  WIPO.

*Primary Examiner*—Lora M. Green
*Attorney, Agent, or Firm*—Morrison & Foerster LLP

[57] ABSTRACT

A method to determine reactivity of a candidate compound with a target receptor which method does not require the physical presence of the receptor is disclosed. By providing a formula for treating data obtained from a reference set of receptors which is predictive of reactivity with the target receptor, the compound to be tested can be physically assessed with respect to the reference receptors, the formula applied, and reactivity with the actual target receptor may be predicted.

9 Claims, 6 Drawing Sheets

| Code | Compound Name |
|---|---|
| | *Amines* |
| A1 | Fendiline |
| A2 | 4,4'-Diaminodiphenyl sulfone |
| A3 | Dipyridamole |
| A4 | Glafenine |
| | *Cephalosporins* |
| C1 | Cephaloglycin |
| C2 | Cephapirin |
| C3 | Cephalothin |
| C4 | Cephradine |
| | *Dyes* |
| D1 | Cibacron brilliant red 3BA |
| D2 | Cibacron brilliant yellow 3GP |
| D3 | 9-(Octadecylamino) acridine |
| D4 | Acridine orange hydrochloride hydrate |
| D5 | Phenyl 9-acridinecarboxylate |
| | *Aliphatics* |
| F1 | 3-Hydroxy-1-methylpiperidine |
| F2 | Fertilysin |
| | *Conjugated Aromatics* |
| J1 | Xanthurenic acid |
| J2 | 2,2'-(1,3-indenediformyl)dibenzoic acid |
| J3 | Citrinin |
| J4 | N-(2-amino-4-chlorophenyl)anthranilic acid |
| J5 | α-Cyano-3-hydroxycinnamic acid |
| J6 | Nalidixic Acid |
| J7 | Lasalocid |
| J8 | Quinaldic acid |
| | *Ketones* |
| K1 | 5,5'-Dibromosalicil |
| K2 | 4,5 Diphenyl-1,3-dioxolan-2-one |

| Code | Compound Name |
|---|---|
| | *Phenols* |
| L1 | Nordihydroguaiaretic acid |
| L2 | Dienestrol |
| L3 | Catechin |
| L4 | Naringenin |
| | *Amides* |
| M1 | 1,3-Di-p-tolyl-2-thiourea |
| M2 | Indomethacin |
| M3 | Colchicine |
| M4 | Nimesulide |
| | *Nitro-aromatics* |
| N1 | 5-(4-nitrophenyl)-2-furoic acid |
| N2 | N-(4-Dimethylamino-3,5-dinitrophenyl)-maleimide |
| N3 | 4,5-Dichloro-2-nitroaniline |
| N4 | 2-(2,4-Dinitrostyryl) thiophene |
| N5 | 1-(5-Nitrofurfurylidine-2-imino)-2,4-dimethyl-5-cyano-6-pyridone |
| N6 | Nitrofurantoin |
| N7 | Furazolidone |
| N8 | 5-Nitro-2-furanacrolein |
| N9 | 5-Nitro-2-furaldehyde diacetate |
| N10 | 5-Nitro-2-furaldehyde semicarbazone |
| N11 | 1,5-Bis-(5-nitro-2-furyl)-1,4-pentadien-3-one |
| N12 | *tert*-Butyl 5-nitro-2-thiophene carboxylate |
| N13 | 4-Nitro-N-(2-thienylmethylene)aniline |
| N14 | N-(5-Nitro-2-pyridyl)-3,4,5,6-tetrachlorophthalamic acid |
| N15 | N-(5-Nitro-3-pyridyl)phthalamic acid |

FIG. 2A

| Code | Compound Name | Code | Compound Name |
|---|---|---|---|
| *Peptides* | | U9 | γ-Oxo-2-naphthalenebutyric acid |
| P1 | γ-Glu-S-hexyl cys-glu | U10 | 2-(4-aminophenoxy)acetic acid hydrochloride |
| P2 | γ-Glu-S-hexyl cys-phenyl gly | U11 | 2-(4-cinnamoylphenoxy)acetic acid |
| P3 | γ-Glu-S-hexyl cys-β-ala | U12 | 2-(4-formylphenoxy)acetic acid |
| P4 | γ-Glu-S-octyl cys-gly | *Xanthenes* | |
| P5 | γ-Glu-S-butyl cys-gly | X1 | Erythrosin B |
| P6 | γ-Glu-S-(β-methyl naphthyl)cys-gly | X2 | phloxine B |
| *Quinones* | | X3 | Fluoresceinamine, isomer II |
| Q1 | 1,2,3,4-Tetrafluoro-5,8-dihydroxy-anthraquinone | X4 | Pyrogallol red |
| Q2 | 6-(Diethylaminomethyl)kojic acid | X5 | Fluorescein isothiocyanate, isomer 1 |
| *Steroids* | | X6 | 9-phenyl-2,3,7-trihydroxy-6-fluorone |
| S1 | 5α-Androstane-3b, 17β-diol hydrate | X7 | 4-(6-hydroxy-3-oxo-3H-xanthen-9-yl)benzoic acid |
| S2 | Cholic acid | X8 | 9-(4-(Dimethylamino)Phenyl)-2,6,7-Trihydoxy-3H-Xanthen-3-One Sulfate |
| S3 | Lithocholic acid | | |
| S4 | Deoxycholic acid | | |
| S5 | Chenodeoxycholic acid | X9 | 6-hydroxy-3-oxo-3H-xanthene-9-propionic acid |
| S6 | Corticosterone | | |
| S7 | Cymarin | X10 | 9-(2,4-Dichlorphenoxymethyl)-6-hydroxy-3H-xanthen-3-One |
| *Triazines* | | | |
| T1 | 2-Decanoyl-4,6-diamino-1,3,5-triazine | X11 | Dimethyl 4-(6-hydroxy-3-oxo-3H-xanthen-9yl) isophthalate |
| T2 | Simazine | *Miscellaneous* | |
| T3 | 4,6-Dihyroxy-1,3,5-triazine-2-acetic acid O-anisidide | Z1 | Pyrocatechol violet |
| | | Z2 | Ajmaline |
| *Unconjugated aromatics* | | Z3 | 6-Chloro-3-nitro-2H-chromene |
| U1 | Ibuprofen | Z4 | Cholecalciferol |
| U2 | Indoprofen | Z5 | 1,1'-Dibenzoylferrocene |
| U3 | Fenoprofen | Z6 | 2,5-Diphenyloxazole |
| U4 | (S)-6-methoxy-a-methyl-2-naphthaleneacetic acid, sodium salt | Z7 | Ethaverine |
| | | Z8 | Econazole |
| U5 | Bis(4-chlorophenoxy)acetic acid | Z9 | Harmaline |
| U6 | Fenbufen | Z10 | Quinine |
| U7 | 2-(4-benzyloxyphenoxy)-2-methylpropionic acid | Z11 | Scopoletin |
| U8 | 2-(4-*tert*-butylphenoxy)acetic acid | | |

FIG. 2B

METHOD TO IDENTIFY BINDING PARTNERS

TECHNICAL FIELD

The invention relates to identification of compounds that are useful in analysis, therapy and other applications where it is desirable to provide a substance which binds specifically to a target molecule. More specifically, the invention concerns a specific pattern-matching technique which permits candidate binding substances to be screened in the absence of the target molecule.

BACKGROUND ART

There are numerous instances in which it is desirable to find a ligand that specifically binds a receptor. To cite the most obvious examples, if the receptor is responsible for activation of a particular type of cell, ligands which bind the receptor may find therapeutic use in either activating or preventing the activation of the receptor, with a corresponding physiological effect on the cell. If the cell is contained in an animal or a plant, the effect may be felt by the entire organism. Thus, a very popular approach to designing new drugs rests on finding appropriate binding agents for these receptors.

Ligands that bind specific receptors can also find applications in analytical contexts. For example, antibodies are members of the generic class "receptors" and are useful components in immunoassay procedures. All of these procedures rely on the specific interaction between an antigen and an antibody; either partner may be the analyte.

In additions separation procedures and other processes with industrial application may take advantage of specific binding. To take a very straightforward illustration, an impurity may effectively be removed from a composition by treating the composition with a solid support to which is bound a "receptor" capable of binding the impurity to the relative exclusion of the other components of the composition, provided the affinity of the receptor for the impurity is sufficiently greater than for the desired components.

In all of the above cases, the amount of affinity that characterizes the specific binding and the degree of specificity required depends on the circumstances. Some applications are benefited by a relatively weak interaction, whereas others require a high affinity. Some applications are more demanding of specificity than others.

The obvious brute force method to find a ligand that will bind a receptor of interest is physically to test the capability of a large number of compounds which are potential ligands with respect to their ability to bind the target receptor. This method would no doubt eventually lead to finding a successful ligand in virtually every case but is clearly more time consuming and labor-intensive than would be desirable for practical utility. First, the receptor must be produced in some physical form that can be tested and sufficient quantities must be provided to test the range of compounds that are candidates. Second, if compounds are tested in just random order, a large quantity of receptor will be needed. This, especially in the case of cellular receptors, may be prohibitively expensive.

Several approaches have been suggested to minimize these difficulties. First, rather than testing compounds at random, a systematically varied panel of compounds could be used. Such systematically varied panels can conveniently be constructed by forming polymers from monomer units of predetermined characteristics. The most convenient such polymers are peptides, but polysaccharides, polynucleotides and the like could also be used. The parameters that are important and the manner of constructing such panels are described in U.S. Pat. Nos. 4,963,263 and 5,133,866, the contents of which are incorporated herein by reference.

In addition to, or instead of, using systematically varied panels of compounds as candidates, the screening itself can be conducted in such a way as to minimize the number of physical measurements that are required. For example, as set forth in U.S. Pat. No. 5,217,869, which is incorporated herein by reference, a reactivity profile for a ligand known to react with a target can be established by providing a standard panel of binding agents. The profile obtained characterizes this particular ligand known to bind the receptor. The candidate compounds can then be tested against the same panel to obtain their corresponding profiles. When a corresponding profile matches that of a ligand known to be a successful binder to the target, the compound which generated the matching profile will have a high probability of binding the receptor. In an alternative, inverse image panels are prepared with varying characteristics, and profiles obtained for the receptor and ligand against opposite panels are matched.

Various other technologies are directed to methods to improve the ease with which the physical binding of receptor to candidate ligand can be measured, such as the use of robotics, fluorescence detection of reactivity, physical arrangements of the panels, and so forth.

Other methods which seek to find specific binding pair members include computer based methods such as three dimensional database searching, x-ray crystallography, molecular modeling, and the like. Other methods employ antibodies as surrogate targets or simply rely on the behavior of the compound with respect to related target receptors. For example, the behavior of a compound as an inhibitor of a particular serine protease, or of a number of serine proteases, might lead one to assume that it will be a useful inhibitor of an additional serine protease for which its inhibition activity has not yet been determined. The validity of this last mentioned method relies on the similarity of the serine proteases that are the "reference receptors" for which the binding characteristics of the test compound are known to the target receptor (serine protease) for which the binding characteristics are not known.

The present invention provides another method to match ligand with a target receptor. It is especially helpful when limited supplies of the target receptor are available. The invention method is especially useful in drug design projects where the target has never been fully purified, is unstable or otherwise not available in adequate quantities for large-scale screening, or when the assay procedure for the target is complex and costly. Further, the method minimizes consumption of receptor in a program of screening against many potential ligands.

DISCLOSURE OF THE INVENTION

The invention utilizes what is, in effect, a surrogate for the receptor to screen an arbitrary number of potential ligands. First, a reactivity binding profile of the target receptor with respect to a "training set" of compounds, preferably having characteristics which are systematically diverse, is prepared. The training set might include, for example, ten different compounds which will have varying degrees of affinity for the target receptor. Thus, the target receptor profile will show a set of varying affinities with these compounds. Rather than test additional candidate ligands with respect to the target receptor itself, a "surrogate" is artificially created by testing the reactivity of this same set of ten training compounds against another panel to which the training set also shows varying degrees of reactivity. This might be called a reference receptor panel. Each compound in the training set will therefore show a pattern of reactivities with respect to this second panel.

This results in a two-dimensional matrix wherein the level of reactivity of each member of the training set with respect to each member of the receptor panel is recorded. The level of reactivity of each member of the reference panel with each of the training compounds is thus simultaneously recorded in an orthogonal dimension.

Each one of the "reference receptors" will, of course, show a different profile with respect to the training set than did the actual target receptor. However, some computational combination, preferably a linear combination, of the these reference receptor profiles will generate a profile which matches as closely as possible that obtained from the target receptor itself. That optimal approximation constitutes a surrogate for the target receptor. The formula which results from the computation with respect to the reference receptors is used to estimate reactivities for newly tested compounds. Empirically, such surrogates have good predictive power when applied to ligands outside the training set. A library of ligand profiles against the reference panel can thus be searched computationally with results comparable to a direct physical screen of the ligands.

Thus, for each compound subsequently tested, reactivity against each member of the reference panel is obtained and the formula derived from the training set is applied to obtain a predicted value with respect to the target receptor. Rather than directly testing the reactivity of a candidate compound with a target, it is possible instead to test its reactivity with respect to a panel of readily available reference receptors, apply the formula to the results, and predict what would have happened had the target receptor itself been used. The larger the library of stored ligand profiles against a reference set, the larger the increase in efficiency for screening by surrogate.

In one aspect, the invention is directed to a method to determine the ability of a candidate compound to react with a target receptor which method comprises providing a surrogate for the target receptor. The surrogate is that formula representing a computational combination, preferably a linear combination, of at least 2 reference reactivity profiles, which best agrees with the empirical binding data of the target against the training set of compounds. The reference reactivity profiles represent the reaction of each member of a panel of reference receptors with respect to a set of compounds, which set of compounds can be designated a "training set". The formula is then applied to the reactivities with respect to each of the members of the panel of reference receptors that is obtained for each candidate compound. The outcome of applying this formula mimics what would be found had the compound been tested directly with the target receptor.

Another aspect of the invention is a particularly preferred combination of a training set and panel of reference receptors. In this preferred matrix, each member of the panel of reference receptors has effectively an inverse image member in the training set of compounds. In this way, the number of panel members and training compounds is minimized by removing redundant overlaps.

BRIEF DESCRIPTION OF THE DRAWINGS

FIGS. 2A–2D show the results obtained when a training set of compounds is tested with respect to a panel of reference receptors to generate a surrogate for a target receptor. The results of testing a multiplicity of additional compounds against the panel of reference receptors and applying the formula defining the surrogate is compared to testing the additional compounds directly against the target receptor. Gray scale indicates $IC_{50}$ values.

FIG. 3b shows the residuals from FIG. 3a.

MODES OF CARRYING OUT THE INVENTION

Figure 1:
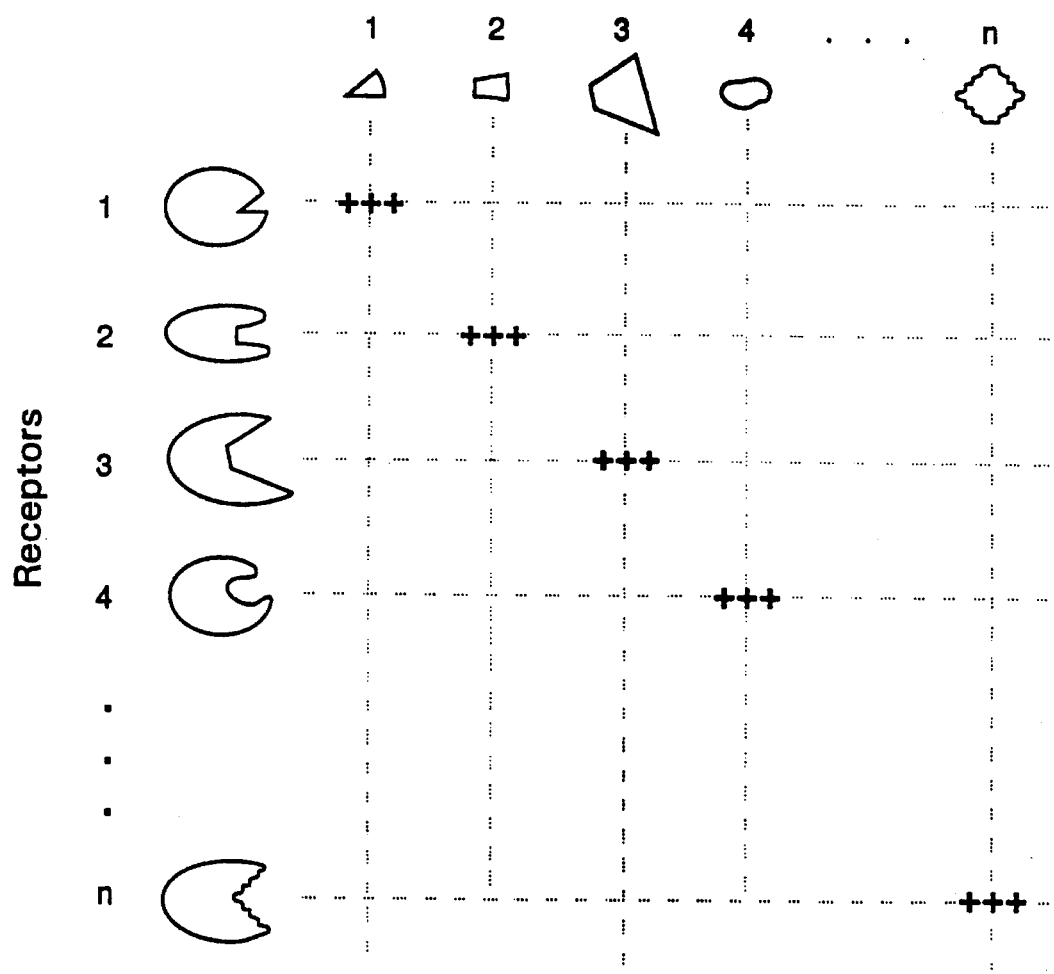
FIG. 1 shows a preferred embodiment of the training set/reference receptor matrix.

The invention permits a large number of candidate compounds to be tested for their ability to react with, and in particular to bind to, a target receptor without necessity for large amounts of the target receptor per se. The target receptor itself is required only in sufficient quantity and purity to generate the formula which creates the surrogate.

As used herein, the term "receptor" includes, for example, molecules that reside on the surface of cells and mediate activation of the cells by activating ligands, but also is used generically to mean any molecule that binds specifically to a counterpart. One member of a specific binding pair would arbitrarily be called a "receptor" and the other a "ligand". No particular physiological function need be associated with this specific binding. Thus, for example, a "receptor" might include antibodies, immunologically reactive portions of antibodies, molecules that are designed to complement other molecules, and so forth. Indeed, in the context of the present invention, the distinction between "receptor" and "ligand" is entirely irrelevant; the invention concerns pairs of molecules which specifically bind each other with greater affinity than either binds other molecules. However, for ease of explanation, the invention method will be discussed in terms of target receptor (again, simply a molecule for which a counterpart is sought that will react or bind with it) and "ligand" simply represents that counterpart.

In order to practice the present invention, the following elements are needed:

First, a reference set of model receptors against which measurable reactivity can be assessed. Various techniques for determining reactivity of compounds with this set of reference receptors are possible, and within the skill of the art. For example, reactivity in the form of binding could be detected by fluorescent label, radioactive label, enzyme label or by an alteration in the properties of the respective ligands by virtue of their binding. It is important to emphasize that it is unnecessary that the reference receptors be in any way related to the target receptor for which they provide a model. For example, in the illustration below, various isoenzymes of glutathione S-transferase (GST) are used as the reference receptors while the actual target is glutathione reductase (GRD). There is no previously discernible similarity between the GSTs of the panel and the GRD that is the target at the levels of primary or tertiary structure or of enzymatic function. One of the advantages of the present invention is that the reference receptors can be quite different in reactivity and in three dimensional structure from the target receptor. The reference panel of receptors may contain as few as 2, but preferably 10–20 and more preferably 20–50 receptors.

Second, a training set of ligands representative of the compounds desired to be further tested with respect to their reactivities with the reference panel is required. If there is a library of compounds to be further tested, a multivariate clustering method can be used to determine representative compounds from the library, or similar to those in the library, for use in the training set. Similarly, compounds with maximally systematically varying properties can also be used. In general, this training set of compounds should include at least as many compounds as the number of reference receptors and preferably about 3 times that number.

Third, there must be enough target receptor available to test the training set empirically, although the target receptor need not be pure. The target receptor must be free of undesired interfering impurities, however.

With these compounds and panels in hand, the profiles of each reference receptor with respect to the training set and the profile of the target receptor with respect to the training set can be obtained by physical measurement. A fourth requirement then is a fitting procedure to match the target's profile with a linear combination of the reference receptor profiles, such as stepwise linear regression. Alternatively, nonlinear fitting techniques can also be used, including neural network techniques. Such mathematical techniques are well understood in the art, and result in the formula which serves as a surrogate for testing of further compounds.

Application of the formula to the profile obtained for a newly tested compound with respect to the reference receptor panel results in an estimate of the ability of the newly tested compounds to bind target. Of course, this represents a probability and not an absolute. The predicted result amounts to a screening procedure to identify compounds with a high probability of binding the target (or not binding the target).

While one compound at a time can be tested with respect to the reference receptor panel and the formula applied to estimate a target reactivity value, the most useful application of the method of the invention pertains to screening libraries of candidate compounds. Thus, quite frequently, a large number of candidate compounds is available and the method of the invention can be used to select those which do and those which do not bind the receptor target. When the method is thus applied to libraries, the results from the newly screened candidates can be added, if desired, to the training set and the process repeated in an iterative loop. Thus, the original training set could be supplemented with selected compounds which are estimated to bind the target receptor strongly and selected compounds which are estimated to bind the target receptor only weakly or undetectably and these compounds used in addition to, or instead of, certain members of the training set to obtain the profiles with respect to reference and actual target receptors. The formula can then be recalculated taking account of these additional members.

Further, not all profiles of the model receptors with regard to the training set need be included, in the end, in the formula. That is, some of the coefficients for model receptor profiles in the linear combination may be zero or negative. Thus, although four model receptors were used for determination of profiles of the training set in the illustration of Example 1 below, only two of these were ultimately used in the formula to calculate the predicted fitted profile and to predict reactivity of the candidates.

The method of the invention can be set forth using a simplified hypothetical matrix, and a linear regression method of combination.

The matrix set forth below represents a hypothetical matrix used to illustrate the generation of the relevant formula as surrogate. Across the top labeled MR1–MR5 are five panel members which represent reference model receptors for the actual target receptor TR. Along the side, labeled TC1–TC5 are five training compounds which bind or otherwise react in varying degrees with each of the reference receptors. The degree of reactivity is arbitrarily assigned a value on a scale of 1–10 where 10 indicates high reactivity and 1 indicates low reactivity.

Sample Matrix

|     | MR1 | MR2 | MR3 | MR4 | MR5 | PR | TR |
| --- | --- | --- | --- | --- | --- | --- | --- |
| TC1 | 6 | 1 | 1 | 7 | 2 | 2 | 2 |
| TC2 | 2 | 4 | 2 | 6 | 2 | 4 | 4 |
| TC3 | 1 | 3 | 8 | 1 | 5 | 6 | 6 |
| TC4 | 5 | 9 | 10 | 10 | 1 | 8 | 8 |
| TC5 | 9 | 1 | 10 | 5 | 9 | 10 | 10 |

In these hypothetical results, profiles for each of the set of training compounds with respect to the reference receptor panel are shown in the horizontal rows and profiles for each reference receptor with respect to the training set of compounds are shown in the vertical columns. Thus, for example, for MR1, there is a moderately high level of reactivity with TC1, low reactivity with TC2, very low with TC3, moderate reactivity with TC4 and very high reactivity with TC5. Thus, each of MR1–MR5 has a particular profile of reactivity with regard to the training set. On the right, marked TR, the target receptor shows a profile against the training set with monotonically increasing reactivities over the TC1–TC5 range, a pattern grossly different from any of the reference profiles.

A formula is then generated by assigning weights to each of the elements of the five MR1–MR5 profiles to obtain a predicted receptor profile that matches that actually obtained for the target receptor. The weighting values will need to be the same for each element of the profiles. Thus, the weights applied to the TC1 element respect to how the values from MR1–MR5 are counted have to be the same as those applied to TC2. Ultimately the algorithm will be of the form $A(MR1)+B(MR2)+C(MR3)+D(MR4)+E(MR5)=$ the value assigned to the predicted value according to the surrogate, shown in the table as PR. Each of the coefficients A–E will have a numerical value; some of the coefficients may be zero. This same equation, with the same values of A–E will be used to calculate the predicted reactivity with the target receptor for any individual candidate compound.

In the above example, $A=+2; B=+3; C=-1; D=-2; E=+1$. Here the coefficients allow a perfect match between the Predicted Receptor (PR) profile and the target receptor (TR) profile with respect to the training set. In general, and if more compounds are included in the training set a perfect match may not be possible; but the closest approximation obtainable is useful to the same end.

Thus, for any new compound, a prediction for reactivity with target is obtained as follows: A profile that provides reactivity values for MR1–MR5 is obtained. The values obtained are then substituted into the formula set forth above, with the predetermined values of A–E. A predicted value is calculated. Thus, a new candidate compound, which gives a profile with values of MR1=8, MR2=9, MR3=4, MR4=7 and MR5=5, will be evaluated according to the formula:

$$(+2)(8)+(+3)(9)+(-1)(4)+(-2)(7)+(+1)(5)=PR$$

to provide a predicted reactivity value of 30. This demonstrates that the method can predict higher reactivity than available in the training set. Confirmed high reactivity compounds can be added to the training set to refine the formula.

Example 1 set forth below indicates that this general approach is successful in predicting the reactivity of any candidate compound with a target; accordingly, no further supplies of target receptor are required in order to test an arbitrary number of compounds.

In a preferred embodiment of the original matrix, both the reference receptor panel and the training set are maximally diverse and represent inverse images. This is illustrated in FIG. 1 which shows a hypothetical matrix of ligands and reference binding agents. As illustrated in the figure, antibody 1 and peptide 1 interact strongly; antibody 2 and peptide 2 do so; antibody 3 and peptide 3, etc. There is relatively weak interaction between, say, peptide 3 and antibody 2 or antibody 1. In effect, the antibody panel (used here in place of the reference receptor panel) and the peptide panel (here used in place of the training set) represent inverse images.

Kits can be prepared which include, in separate containers, each of the members of the training set, each of the members of the reference receptor panel, and the target receptor, along with reagents for testing their reactivity.

The following example is intended to illustrate but not to limit the invention.

EXAMPLE 1

In this example, the reference receptors whose profiles will be obtained with respect to a training set of compounds were isoenzymes of glutathione s-transferase (GST). The panel of reference receptors containing ten such isoenzymes is shown at the top of the FIGS. 2A–D. The target receptor in this example was glutathione reductase (GRD) shown at the right of FIGS. 2C and 2D. The first 20 compounds listed on the left were used as a training set and, when tested for binding to glutathione reductase, generated the profile marked GRD at the right. In this "gray scale", the darker the square, the more tightly the compound is bound; the lighter, the less tightly bound. The list of compounds and abbreviations is provided at FIGS. 2A and 2B.

For the reference receptors, GSTs A1-1, P1-1, M1$a$-1$a$ and M2-2 were provided as recombinant human enzymes; R1-1, R8-18 are rat enzymes of the alpha class; R1(25)-8 is a site-directed mutant of R8-8. HF2 and HF3 are house fly GST enzymes purified by hexyl-glutathione affinity chromatography from cell lines provided by M. Syvanen at UC Davis; Schistosome GSTS1 is available from Pharmacia as part of a fusion protein cloning vector. Yeast glutathione reductase was purchased from Sigma.

In order to test the degree of binding between GSTs and the compounds on the left of the table, five serial 5-fold dilutions from 250 μM to 0.4 μM were tested and the 50% inhibition concentration ($IC_{50}$) was calculated from a curve fitted to the data. For compounds with an estimated $IC_{50}$ below 0.4 μM, additional dilutions were tested until the true $IC_{50}$ was bracketed. Four of the GSTs and 20 compounds were selected as maximally diverse. The $IC_{50}$s are indicated in the figure on a scale of from less than 0.4 μM; less than 2.0 μM, less than 10.0 μM, less than 50 μM, less than 250 μM, and less than 1000 μM. Thus, $IC_{50}$s of less than 0.4 μM would appear black on this scale; those with $IC_{50}$s of less than 1000 μM would appear white. Intermediate values are varying shades of gray.

Figure 2C:
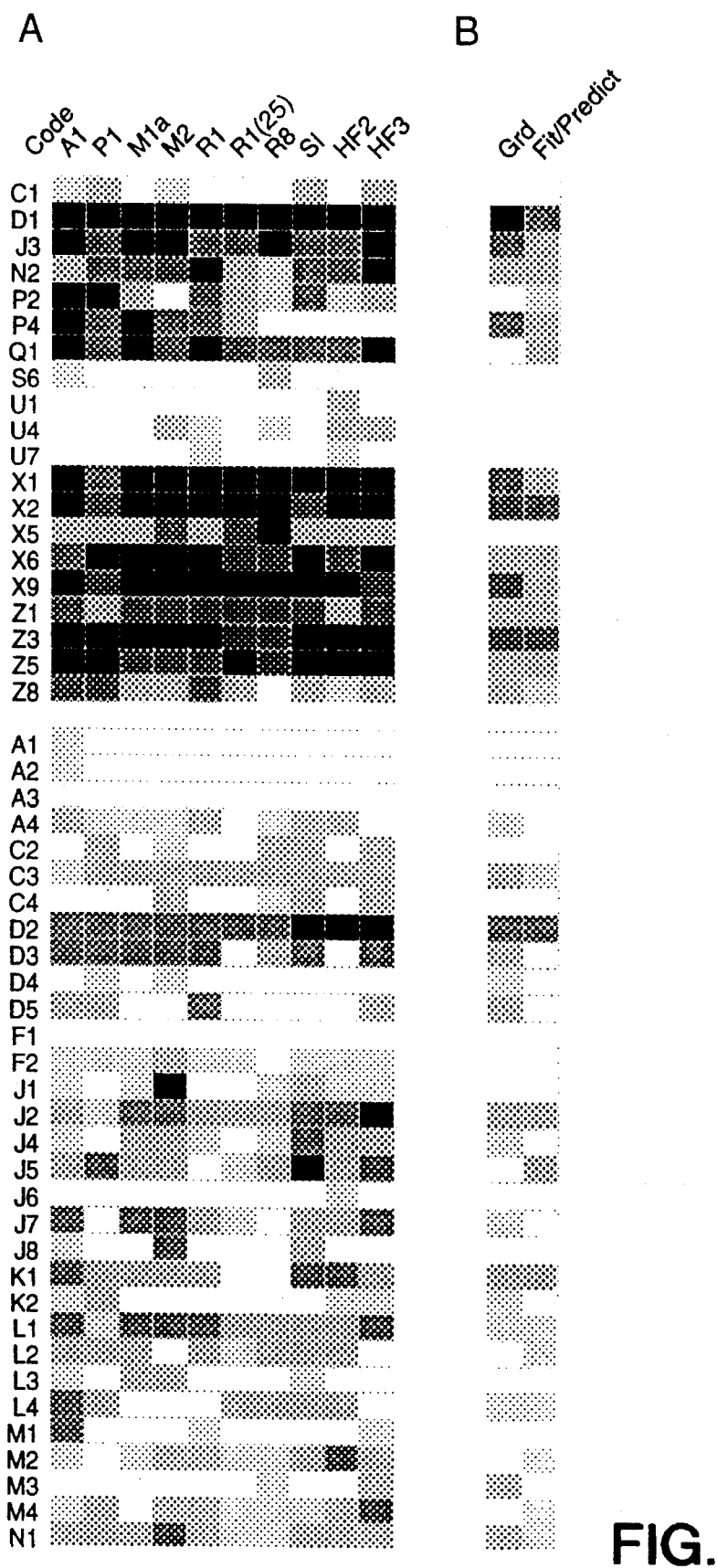
Figure 2D:
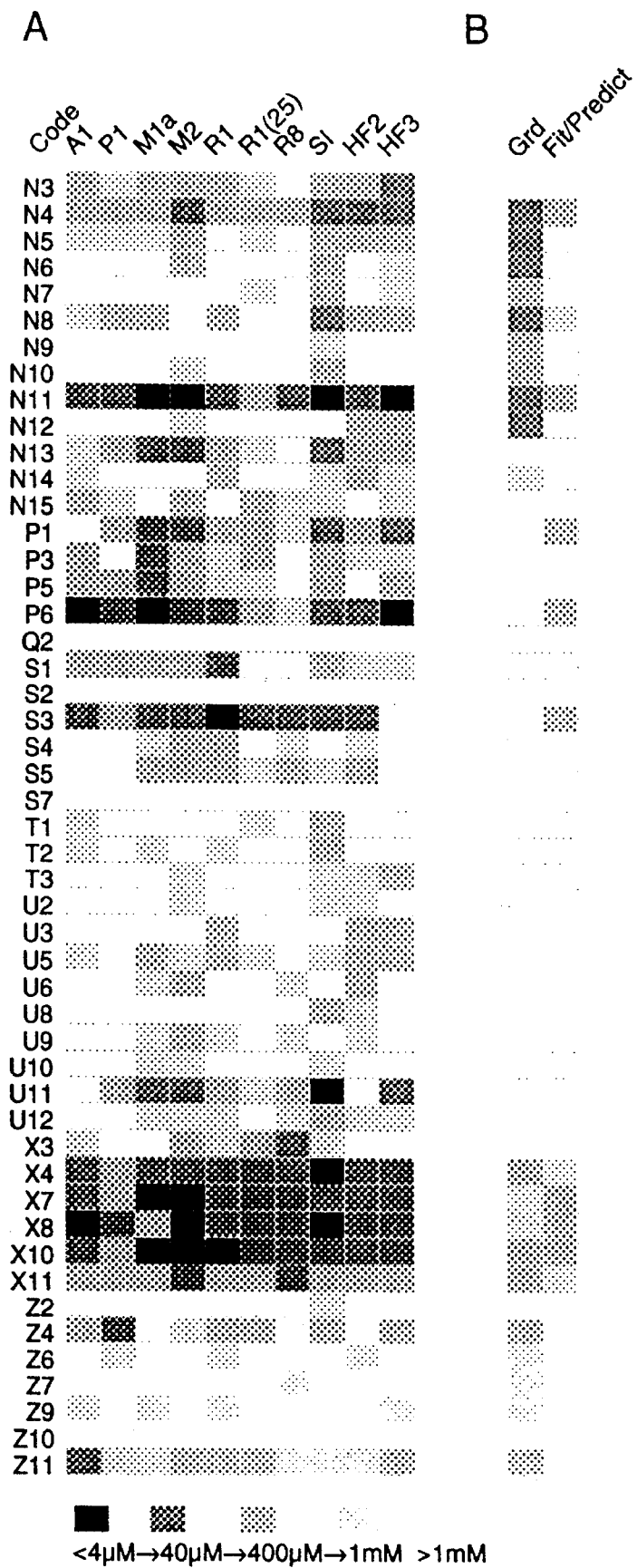
Figure 3A:
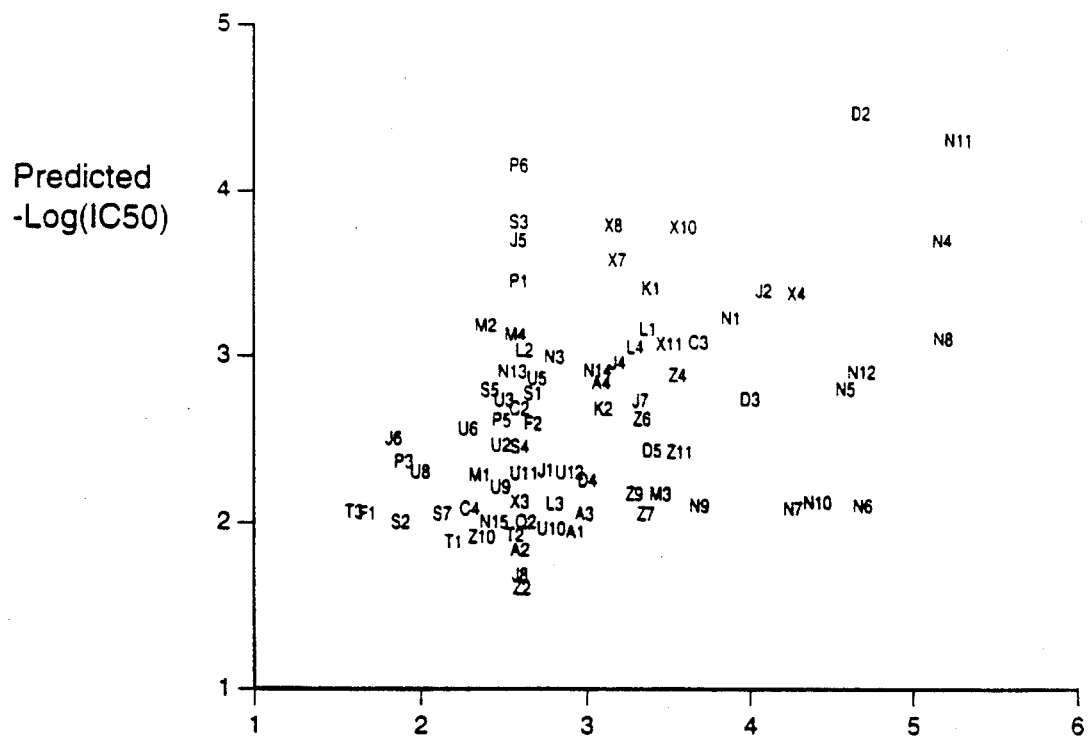
FIG. 3a shows the predictions and actual empirical data from FIG. 2 as a scatter plot indicating high degree of correlation.
Figure 3B:
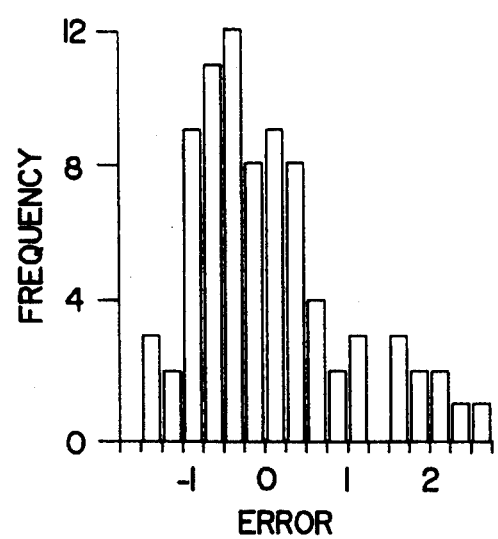

The column marked "Fitted Predicted Values" in FIGS. 2C and 2D is obtained by a linear combination of the results for the four enzymes used in the panel of reference receptors tested against the 20 compounds that come first in the chart. This same fitting combination was then used to predict GRD binding to the remaining compounds. The predicted results are compared with the actual results against target on the right-hand columns of the figure. A good correlation is obtained; the regression coefficient is 0.8 with a dispersion factor of 0.7, as shown in FIGS. 3$a$ and 3$b$. FIG. 3$a$ shows the data for the 80 test compounds of FIGS. 2A–2D not used in the fitting procedure and FIG. 3$b$ shows the residuals (experimental-predicted) from FIG. 3$a$.

The mathematical form for the linear regression is:

$$\log(IC_{50})_{i,T} = \sum_{j=1}^{n} C^{Rj} \log(IC_{50})_{i,Rj}.$$

The successful correlation obtained above may be surprising since the GRD derived from yeast is a NADPH dependent protein which has a different enzymatic function from GST. These enzymes share no sequence homology, and comparison of the crystal structures of GST and GRD reveals no tertiary structural similarities.

We claim:

1. A method to determine a predicted reactivity of a candidate compound with a target receptor, which method comprises the steps of:

(a) providing a formula that represents a combination of the reactivity profiles of at least two members of a panel of reference receptors with respect to a first set of training compounds, which formula calculates a predicted profile that best matches the reactivity profile of the target receptor with respect to said first set of training compounds;

(b) determining the reactivity of said at least two members of the panel of reference receptors with a candidate compound to obtain a reactivity profile for said candidate compound with respect to said members of said panel; and (c) calculating the predicted reactivity of the target receptor for said candidate compound by applying said formula of step (a) to the reactivity profile of the candidate compound determined in step (b) to predict the reactivity of the candidate compound with the target receptor.

2. The method of claim 1 wherein the first set of training compounds and the panel of reference receptors are inverse image panels.

3. The method of claim 1 wherein the first set of training compounds and the panel of reference receptors are each maximally diverse.

4. The method of claim 1 wherein the panel of reference receptors is maximally diverse.

5. The method of claim 1 wherein the reactivity profiles in step (b) are determined with respect to each member of a library of candidate compounds.

6. The method of claim 1 wherein the reactivity profiles in step (b) are determined with respect to each member of a library of candidate compounds, and wherein application of step (c) results in compounds which are estimated to react well and compounds that are estimated to react poorly with a target receptor.

7. The method of claim 1 wherein the combination in (a) is a linear combination.

8. The method of claim 6 wherein at least some of the compounds which are estimated to react well and at least some of the compounds which are estimated to react poorly with the target receptor are added to the first set of training compounds to obtain an expanded set of training compounds, and step (a) is repeated with said expanded set of training compounds to obtain an improved formula.

9. The method of claim 8 which further includes (d) determining the reactivity of said at least two members of said panel of reference receptors with a candidate compound to obtain a reactivity profile for said candidate compound with respect to said members of said panel; and (e) calculating the predicted reactivity of the target receptor for said candidate compound by applying said formula of step (a) to the reactivity profile of the candidate compound determined in step (d) to predict the reactivity of the candidate compound with the target receptor.

* * * * *